US007935233B2

United States Patent
Moon et al.

(10) Patent No.: US 7,935,233 B2
(45) Date of Patent: May 3, 2011

(54) TYROSINASE ENZYME ELECTRODE AND PRODUCTION METHOD THEREOF

(75) Inventors: Seung-Hyeon Moon, Gwangju (KR); Gha-Young Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 470 days.

(21) Appl. No.: 11/976,738

(22) Filed: Oct. 26, 2007

(65) Prior Publication Data
US 2009/0250343 A1 Oct. 8, 2009

(30) Foreign Application Priority Data
Apr. 2, 2007 (KR) .................. 10-2007-0032398

(51) Int. Cl.
G01N 27/327 (2006.01)
C12N 11/02 (2006.01)
C12Q 1/00 (2006.01)

(52) U.S. Cl. ......... 204/403.14; 204/403.04; 204/403.01; 435/177; 205/777.5

(58) Field of Classification Search ......... 204/403.01–403.14, 292, 293; 435/177; 205/777.5
See application file for complete search history.

(56) References Cited

OTHER PUBLICATIONS

Vidal et al. (Talanta 68 (2006) 791-799, pub. Aug. 22, 2005).*
Nakamura et al. (Analytical Sciences, Sep. 2006, vol. 22, 1261-1264).*
Gooding et al. (Electroanalysis 2003, 15, No. 2, 81-96).*
Kim et al. (Anal. Chem., 2006, 78 (6), pp. 1913-1920).*

* cited by examiner

*Primary Examiner* — Alexa D Neckel
*Assistant Examiner* — Jennifer Dieterle
(74) *Attorney, Agent, or Firm* — The Nath Law Group; Tanya E. Harkins; Mihsuhn Koh

(57) ABSTRACT

Disclosed are a tyrosinase enzyme electrode containing metal nanoparticles and its producing method. Metal nanoparticles are applied to a surface of a support with high chemical stability. Also, a buffer layer consisting of a self-assembled monolayer is formed on the metal nanoparticles. Such self-assembled monolayer is used to immobilize tyrosinase enzyme which was subsequently prepared. In other words, the self-assembled monolayer is arranged between the metal nanoparticles and the tyrosinase enzyme so as to immobilize the tyrosinase enzyme on the support. Introduction of the metal nanoparticles into the electrode contributes to improvement in detection limits of the tyrosinase enzyme electrode. In addition, the introduction of substrate induces the activation of enzyme.

5 Claims, 10 Drawing Sheets

TYROSINASE ENZYME ELECTRODE AND PRODUCTION METHOD THEREOF

CROSS REFERENCE TO RELATED APPLICATIONS

This application claims the benefit of the filing dates of Korean Patent Application No. 2007-0032398, filed on Apr. 2, 2007, and No. 2007-0058286, filed on Jun. 14, 2007, both of which are hereby incorporated by reference in there entirety.

BACKGROUND OF THE INVENTION

1. Field of the Invention

The present invention is directed to enzyme electrodes for measurement of residual agricultural chemicals, sometimes, referred to as "residual pesticides". The present invention is also directed to a tyrosinase enzyme electrode containing metal nanoparticles and methods of producing such electrodes.

2. Background Art

Conventional analysis methods for residual agricultural chemical components present in agricultural products, drinking water, etc. include: GC (gas chromatography), GC/MS (gas chromatography/mass spectroscopy), LC (liquid chromatography), LC/MS (liquid chromatography/mass spectroscopy) and the like. Such methods require complicated pre-treatments of samples and a long time for subsequent analysis. The above methods are therefore not applicable to real time measurement.

In order to overcome the problems described above, a variety of measurement methods have been developed. Korean Patent Gazette No. 171159 provides an illustrative example of one measurement method, wherein phenol waste is removed using thermal resistant tyrosinase. This method comprises converting phenol into tyrosine, precipitating the converted tyrosine in a medium and separating the precipitated tyrosine from the medium, which is different from techniques for detection of agricultural chemical components.

Further, Japanese Patent Application No. 2003-159422 (Publication No. 2004-361220) discloses a device for detecting residual agricultural chemicals. The existence of residual agricultural chemicals in a sample are detected by determining characteristics of an LC resonator based on a changeable dielectric constant of the sample, however, this publication does not describe technical methods to improve measurement sensitivity of the residual agricultural chemicals.

In addition, Japanese Patent Application No. 2004-89137 (Publication No. 2005-270008) discloses an analysis method for residual agricultural chemicals, describing a method for high sensitivity detection of carbamate based agricultural chemicals. However this method only has the ability to detect a limited number of species of agricultural chemical components which are present.

As described above, conventional methods for detection of residual agricultural chemicals still have a problem of limited sensitivity and/or measurement range.

BRIEF SUMMARY OF THE INVENTION

The present invention is directed to a tyrosinase enzyme electrode that can easily analyze residual agricultural chemicals or pesticides contained in a subject with accurate detection limits. The present invention is further directed to a method for producing a tyrosinase enzyme electrode.

The present invention is directed to a tyrosinase enzyme electrode comprising; a support; a metal nanoparticle layer formed on the support, the metal nanoparticle layer comprising metal nanoparticles; a buffer layer formed on the nanoparticle layer; and a tyrosinase enzyme formed on the buffer layer, wherein the buffer layer comprises a self-assembled monolayer to immobilize the tyrosinase enzyme.

In some embodiments of the present invention, the metal nanoparticle layer comprises metal nanoparticles in a discrete form, wherein the metal nanoparticles are separated from adjacent nanoparticles, and wherein the nanoparticles are selected from the group consisting of gold, silver, copper, palladium, platinum and combinations thereof.

In some embodiments of present invention, the self-assembled monolayer comprises alkanethiol compounds having functional groups selected from the group consisting of a carboxyl group, amino group, hydroxyl group, sulfonic acid group and combinations thereof. In some embodiments of the present invention, the tyrosinase enzyme is immobilized on the self-assembled monolayer with a coupling agent comprising a diimide group. In further embodiments of the present invention, the support comprises glassy carbon.

The present invention is also directed to a method of producing a tyrosinase enzyme electrode comprising; forming a metal nanoparticle layer on a support, the metal nanoparticle layer comprising metal particles, wherein the metal nanoparticles exist in a discrete form, wherein each nanoparticle is separated from adjacent nanoparticles; forming a buffer layer on the metal nanoparticle layer; and adding a coupling agent, wherein the coupling agent immobilizes the tyrosinase enzyme on the buffer layer.

In some embodiments of the present invention, the nanoparticles are selected from the group consisting of gold, silver, copper, palladium, platinum and combinations thereof. In some further embodiments of present invention, the buffer layer comprises a monolayer, wherein the monolayer is formed by a self-assembly process, and wherein the monolayer comprises alkanethiol compounds having functional groups selected from the group consisting of carboxyl group, amino group, hydroxyl group, sulfonic acid group and combinations thereof.

In some embodiments of the method of the present invention, the tyrosinase enzyme is immobilized on the self-assembled monolayer by a coupling agent comprising a diimide group.

The present invention is further directed to a tyrosinase enzyme electrode comprising an electrode; a metal nanoparticle layer formed on the electrode; a buffer layer formed on the nanoparticle layer; a substrate bound on the buffer layer; and a tyrosinase enzyme immobilized on the substrate. In some embodiments of the present invention, the metal nanoparticle layer comprises metal nanoparticles in a discrete form wherein, each of the metal nanoparticles is separated from adjacent nanoparticles, and wherein the nanoparticles are selected from the group comprising gold, silver, copper, palladium, platinum and combinations thereof.

In some further embodiments of the electrode of the present invention, the buffer layer comprises an alkanethiol compound having a functional group selected from the group consisting of a carboxyl group, amino group, hydroxyl group, sulfonic acid group and combinations thereof. In some embodiments of the present invention, the substrate comprises pyrroloquinoline quinone. In some embodiments the electrode comprises a second substrate, wherein the second substrate comprises pyrroloquinoline quinone which is introduced on the immobilized tyrosinase enzyme. In some embodiments the electrode of comprises glassy carbon.

The present invention is also directed to a method of making a tyrosinase enzyme electrode comprising the steps of: forming a metal nanoparticle layer on an electrode, the metal nanoparticle layer comprising metal nanoparticles; wherein the metal nanoparticles exist in a discrete form, and each of the nanoparticles is separated from adjacent nanoparticles; forming a buffer layer on the metal nanoparticle layer; forming a substrate on the buffer layer; and immobilizing a tyrosinase enzyme on the substrate. In some embodiments of the present invention the electrode comprises a second substrate introduced on the immobilized tyrosinase enzyme. In some embodiments of the invention the second substrate is pyrroloquinoline quinone.

The present invention described above is further illustrated by the following non-limited examples, which are not intended to limit or restrict the scope of the invention but are illustrative embodiments of the present invention.

BRIEF DESCRIPTION OF THE DRAWINGS/FIGURES

FIGS. 8a to 8e schematically depict sequential cross sectional views of tyrosinase enzyme electrode production according to an embodiment of the present invention.

Figure 9:
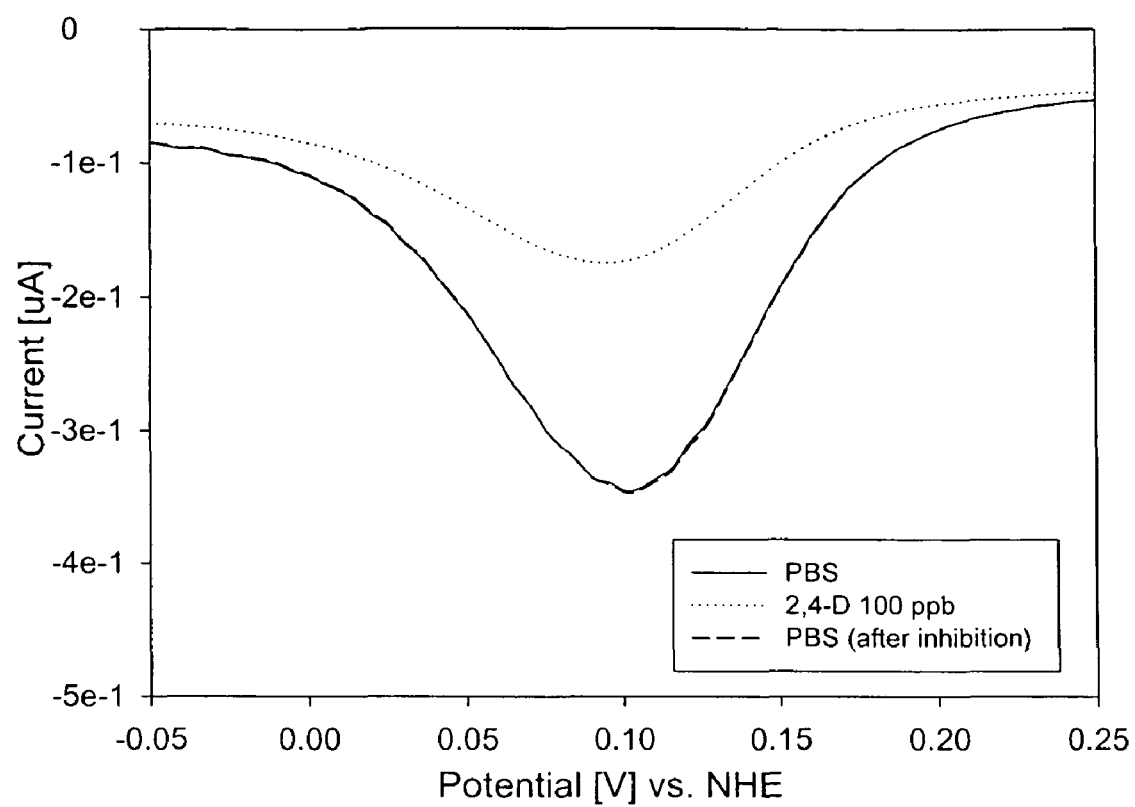

FIG. 9 is a graph depicting the current variation of a tyrosinase enzyme electrode depending on the presence of the residual agricultural chemicals according to an embodiment of the present invention.

Figure 10:
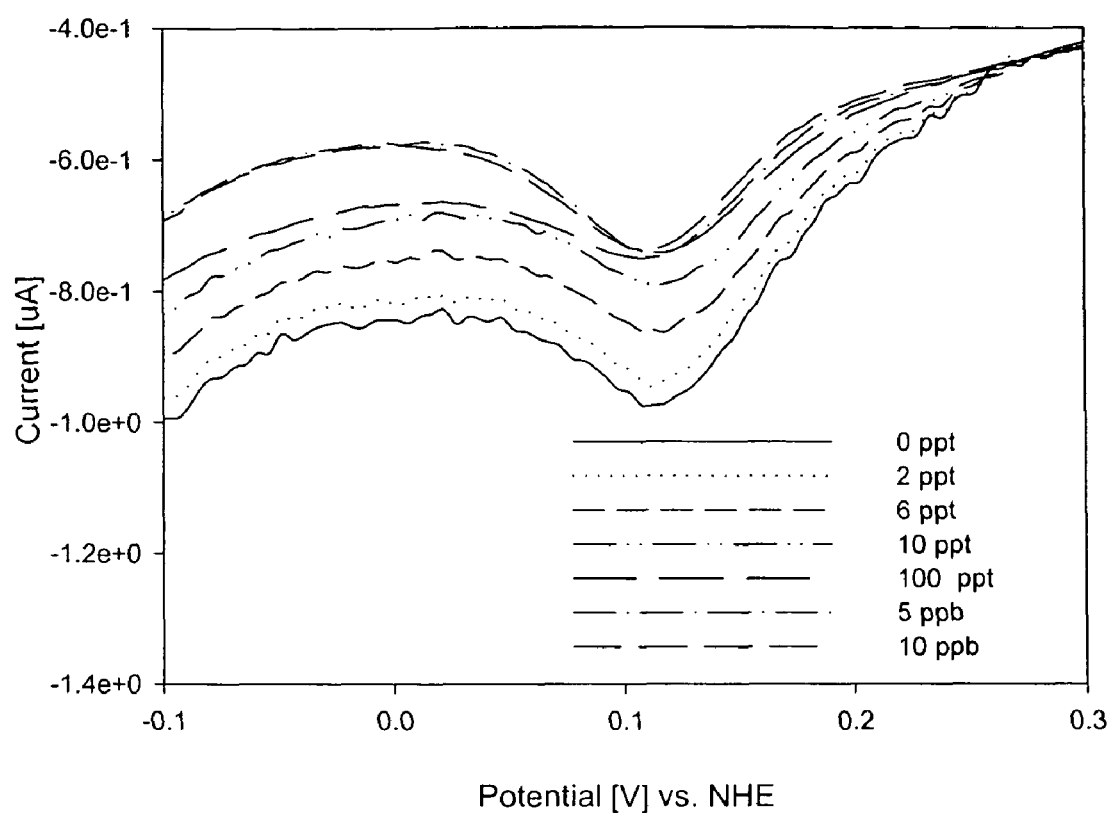

FIG. 10 is a graph depicting the current variation of a tyrosinase enzyme electrode depending on the concentration of 2,4-D according to an embodiment of the present invention.

Figure 11:
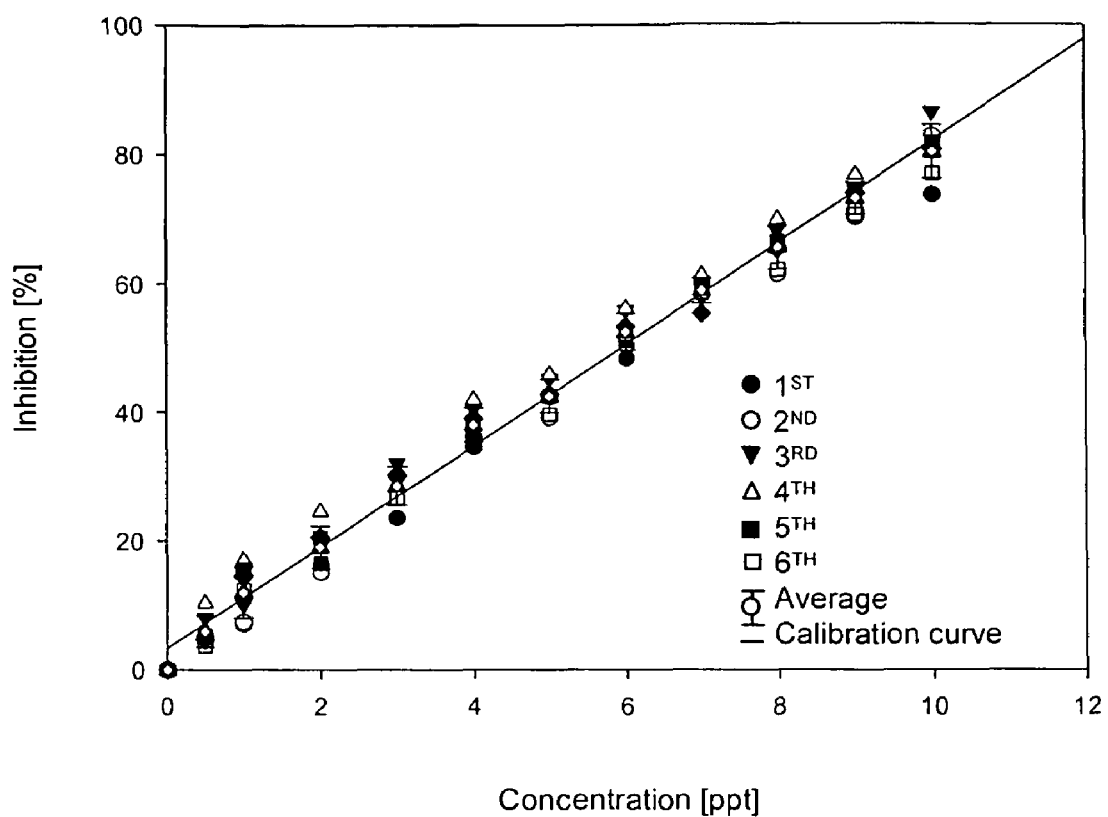
Figure 12:
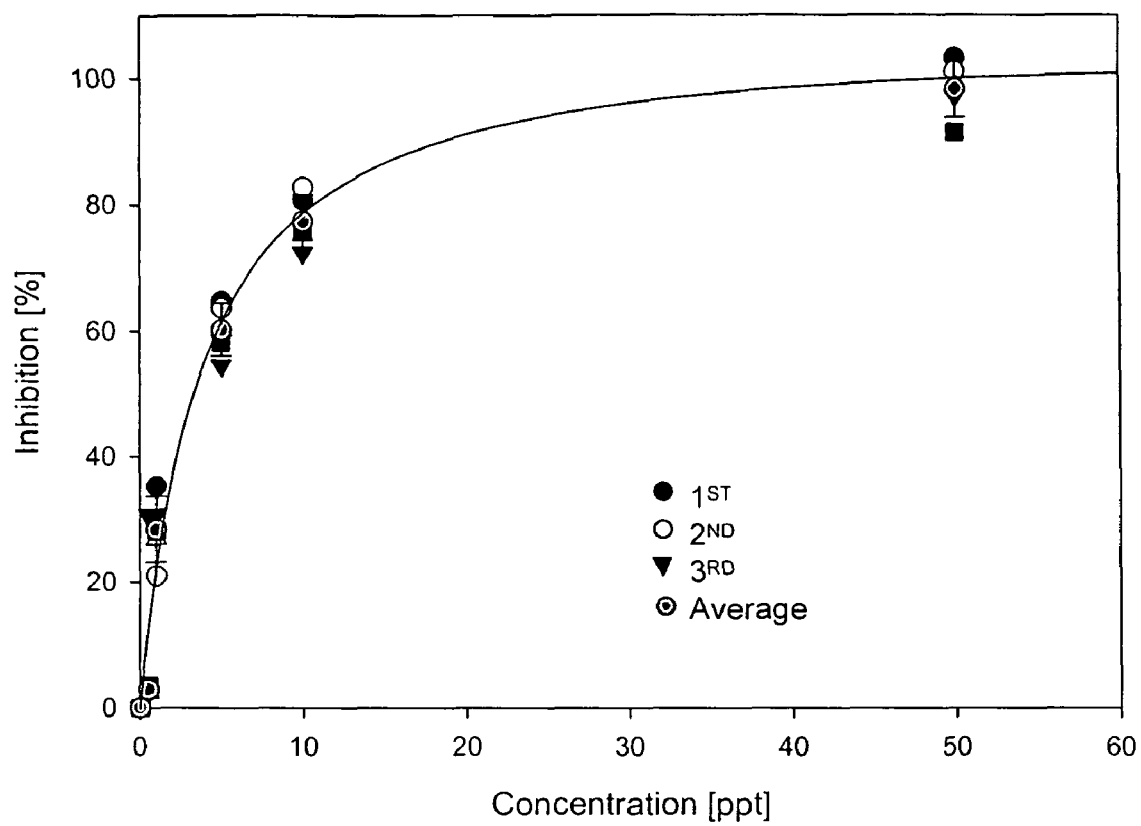

FIG. 11 is a graph depicting the inhibition percentage of a tyrosinase enzyme electrode depending on the concentration of 2,4-D under a constant flow according to an embodiment of the present invention;

FIG. 12 is a graph depicting the inhibition percentage of a miniaturized tyrosinase enzyme electrode with the injection of 2,4-D in a concentration of 0 to 50 ppt (parts per trillion).

DETAILED DESCRIPTION OF THE INVENTION

Tyrosinase is an enzyme, which oxidizes compounds such as phenol, catechol, dopamine, di-catechin, chlorogenic acid, D-dopa, L-dopa, pyrogallol and the like in the presence of oxygen. Previously tyrosinase was known to be inhibited by pesticides such as atrazine or ziram. Thus, specific residual agricultural chemicals as well as phenol and catechol can be measured by the use of a tyrosinase enzyme electrode.

Reaction Scheme 1, illustrates a typical enzyme and electrode reaction of phenol at a tyrosinase enzyme electrode:

Reaction Scheme 1

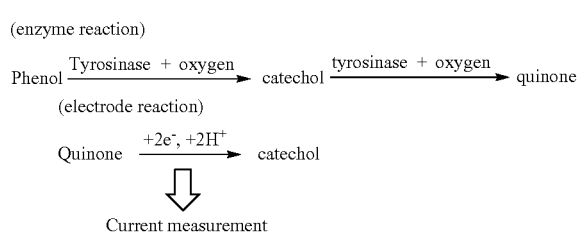

In Reaction Scheme 1, phenol is oxidized into catechol by tyrosinase in the presence of dissolved oxygen, followed by the oxidation of catechol into quinone. The quinone is highly electroactive and easily reduced to catechol. Thus, the concentrations of phenol and catechol can be determined from a calibration curve between the measured current and the concentration of the introduced phenol and/or catechol which is obtained under a constant voltage applied.

Reaction Scheme 2 illustrates the enzyme and electrode reaction at a tyrosinase enzyme electrode in the presence of agricultural chemicals:

Reaction Scheme 2

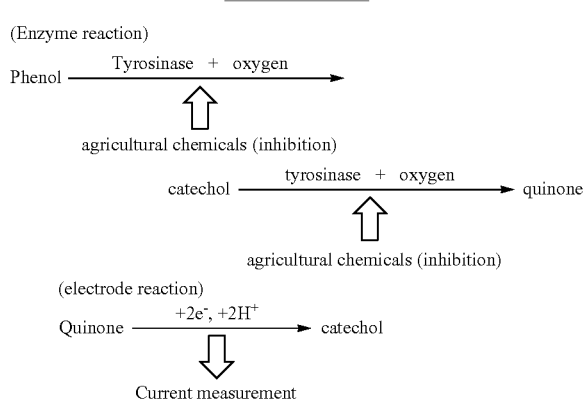

In Reaction Scheme 2, the enzyme reaction is inhibited by the presence of agricultural chemicals. The current is also decreased, attributed to the reduction of the amount of catechol and quinone. Therefore, the concentration of the residual agricultural chemicals can be determined by comparing the currents measured in the absence and presence of the residual agricultural chemicals. Herein, the inhibition percentage is calculated by the following Equation 1:

Inhibition (%)={(current before the addition of agricultural chemicals−current after the addition of agricultural chemicals)/current before the addition of agricultural chemicals}×(100)

Figure 1A:
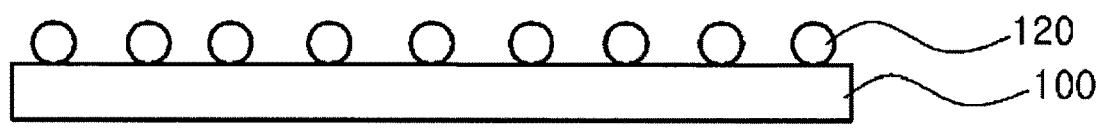
FIGS. 1a to 1c depict cross sectional views sequentially depicting the production of a tyrosinase enzyme electrode according to an embodiment of the present invention.
Figure 1B:
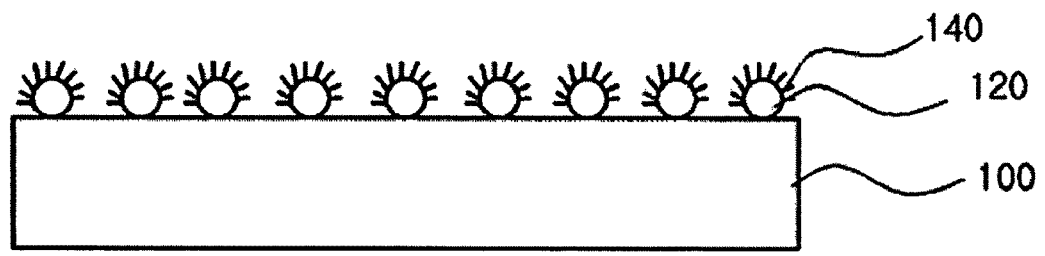
Figure 1C:
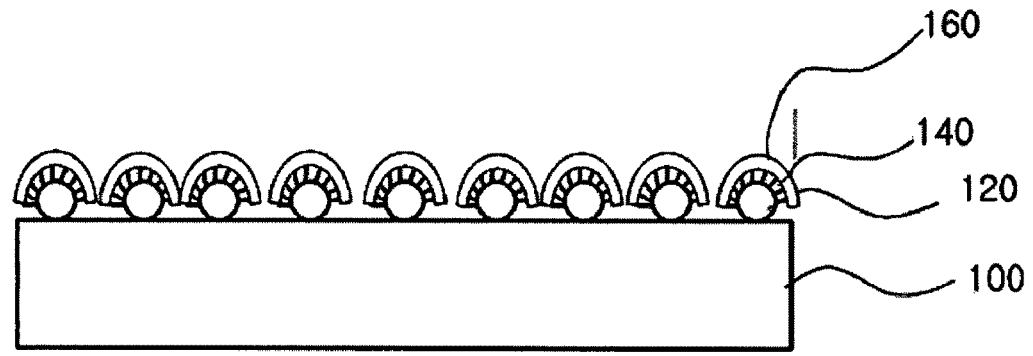

Methods of producing the enzyme electrode are described in as follows: FIGS. 1a, 1b and 1c are cross sectional represents the sequential production of a tyrosinase enzyme electrode according to an embodiment of the present invention. FIG. 1a, depicts a metal nanoparticles layer (120) which is formed on a support (100). In some embodiments, the support (100) is made of materials with excellent chemical stability, and in further embodiments of the present invention the support comprises glassy carbon. In some embodiments, metal nanoparticles formed on the support (100) are selected from the group consisting of gold, silver, copper, palladium, platinum and combinations thereof. In some embodiments the nanoparticle layer (120) comprises nanoparticles in a discrete form, wherein each of nanoparticles is physically separated from adjacent nanoparticles.

In some embodiments of the present invention, gold is used as the nanoparticle. Using gold colloidal particles in a solution results in formation of nuclei on glassy carbon. The formed nuclei are changed into gold nanoparticles on the glassy carbon. That is, gold nanoparticles may be formed by application of pulses in two stages and electro-deposition.

Figure 2:
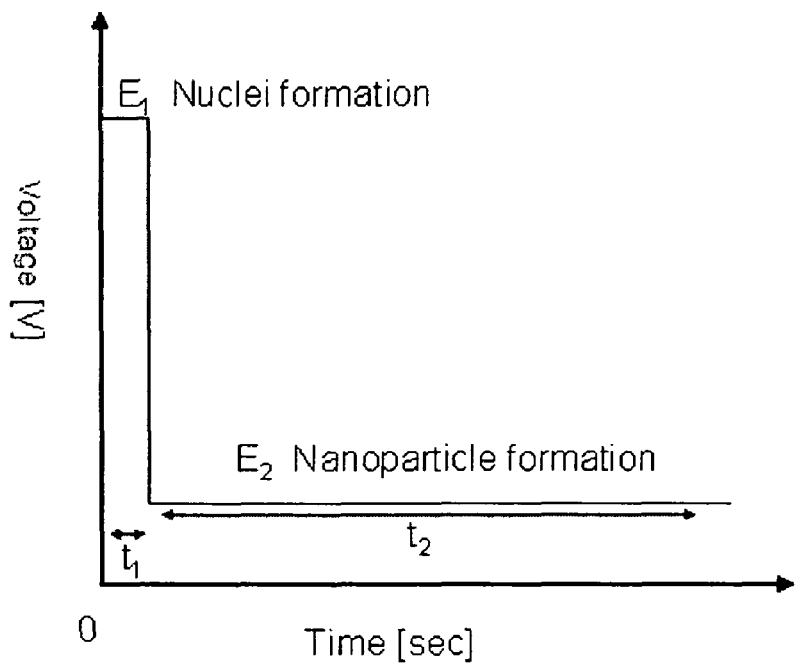
FIG. 2 depicts a graph of the process of forming gold nanoparticles with different voltages applied in two stages, $t_1$ and $t_2$, and regulating size of the nanoparticles and coverage of the nanoparticles.

FIG. 2 illustrates a process of forming gold nanoparticles with different voltages applied in two stages ($t_1$ and $t_2$) thereby regulating the size of the nanoparticles and coverage of the nanoparticles.

In FIG. 2, the working electrode is a glassy carbon, and a platinum electrode and silver/silver chloride electrode which are adopted as an auxiliary electrode and a reference electrode, respectively. About 0.2 mM $KAuCl_4$ is dissolved in nitrogen saturated in about 0.5 M sulfuric acid solution. The process is carried out by controlling applied voltages and times to about 1.0 volt or more and within about 1 second for the first stage, and, to about 1.0 volt or less and about 60 seconds for the second stage, respectively, in relation to the silver/silver chloride based reference electrode.

Accordingly, gold nuclei are formed on the glassy carbon in the first stage and the formed nuclei are grown to nanosized particles in the second stage.

In the process depicted in FIG. 1b, a buffer layer (140) is formed on the support (100) with the nanoparticle layer (120). The buffer layer is disposed between the nanoparticle layer (120) and the tyrosinase enzyme which was subsequently prepared, in order to immobilize the enzyme on the support (100). In some embodiments the buffer layer (140) comprises a monolayer, which is formed by a self-assembly process.

In some embodiments of the present invention, when the support (100) with the nanoparticle layer (120) is precipitated in a solution containing organic silicon, thiol based organic materials, amine based organic active materials, etc., such organic materials are self-assembled to the support (100) to form an ultrathin monolayer. The above film formation process is called a "self-assembly method."

In some embodiments of the present invention, the self-assembly method uses a surfactant comprising a head part, a body part and a tail part, characterized in that the head part is chemically combined with the support (100), the body part interacts with molecules and/or with the support (100) by van der Waals force, and the tail part plays a role of functional group at end of a molecule.

In some embodiments of the present invention, the functional group at the end determines the surface properties of the self-assembled monolayer, which forms the buffer layer (140) and, additionally, is used to immobilize other organic materials or bio-chemically active materials on the support.

In some embodiments of the present invention, an illustrative examples of organic materials used for immobilization of bio-chemically active materials include an alkanethiolate compound having a carboxylic acid as the functional group, wherein the head part of thiol group can be self-assembled to the nanoparticle layer (120) on the support (100) and the carboxylic acid functional group can be used to immobilize the bio-chemically active material, e.g. tyrosinase enzyme, on the support.

In some embodiments of the present invention, the nanoparticle layer (120) is selected from the group consisting of gold, silver, copper, palladium and/or platinum and combinations thereof. In some embodiments, the buffer layer (140) consisting of a self-assembled monolayer is formed on the nanoparticle layer (120). Such a self-assembled monolayer comprises, alkanethiol compounds having functional group selected from the group consisting of carboxyl group, amino group, hydroxyl group, sulfonic acid group and combinations thereof.

In some embodiments (as depicted in FIG. 1c), tyrosinase enzyme (160) is introduced into the buffer layer (140) consisting of the self-assembled monolayer and, in turn, is immobilized. In some further embodiments, in order to immobilize the tyrosinase enzyme (160), a coupling agent having diimide group is used. For example, a self-assembled monolayer having a carboxyl group is added to a combined solution including 0.02 M EDC (N-ethyl-3-(dimethylaminopropyl)carbodiimide-HCl) and 0.05 M NHS (N-hydroxy succinimide), followed by incubation thereof at about room temperature for about 1 hour. Thereafter, a tyrosinase enzyme solution dissolved in a phosphate buffer solution (about 0.1 M at about pH 7) is added dropwise to the incubated solution, which further undergoes the immobilization process at about 4° C. for about 24 hours. The immobilization leads to formation of covalent bonds between tyrosinase and carboxyl group of the self-assembled monolayer.

EXAMPLES

Example 1

Determination of Voltage in Inhibition Percentage Analysis (or Diagnosis)

Figure 3:
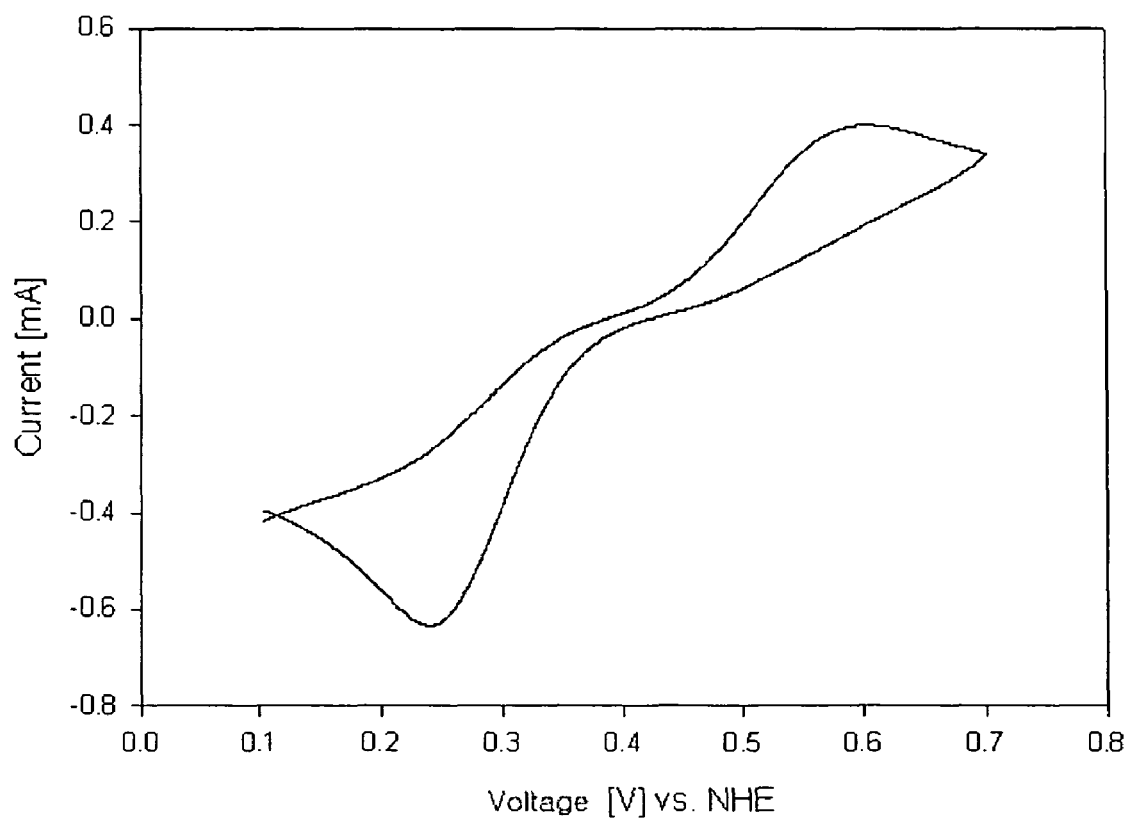
FIG. 3 depicts a cyclic voltammogram of the fabricated tyrosinase enzyme electrode for 1 mM catechol in a phosphate buffer solution.

Applied voltage can be determined by measuring cyclic voltammetry. As such FIG. 3 depicts a cyclic voltammogram of the fabricated enzyme electrode for 1 mM catechol in a phosphate buffer solution with a scan rate of 25 mV/s where the tyrosinase enzyme electrode comprises gold nanoparticles. As shown in FIG. 3, high reduction current at 0.25 V vs. normal hydrogen electrodes (NHE) resulted in reduction of quinone as a product of the tyrosinase-catechol reaction. Therefore, the above voltage (0.25 V) was applied in the analysis of the inhibition percentages of residual agricultural chemicals at the tyrosinase electrode.

Example 2

Determination of Substrate Concentration in Inhibition Percentage Analysis

Figure 4:
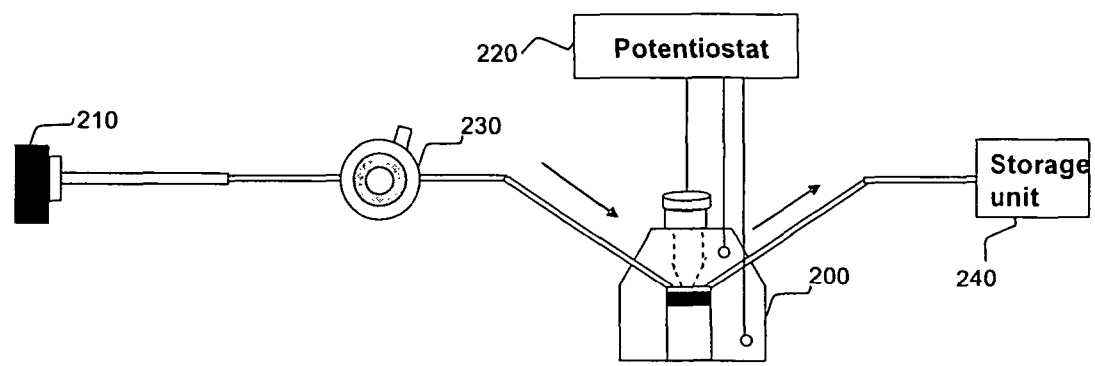
FIG. 4 depicts a flow system for real time measurement of residual agricultural chemicals (or residual pesticides).

For real time measurement of the residual agricultural chemicals, a flow system was constructed as shown in FIG. 4. After assembling the enzyme electrode within an electrochemical cell (200) with a volume of about 53 μl, a phosphate buffer solution (0.1 M, pH 7) was added to the cell using a syringe pump (210) while regulating flow rate of the solution to about 1.2 mL/min. The current was measured by introducing about 5 μl of catechol in varied concentrations through an injection loop (230) while applying voltage of 0.25V to the electrochemical cell using a potentiostat (220).

Figure 5:
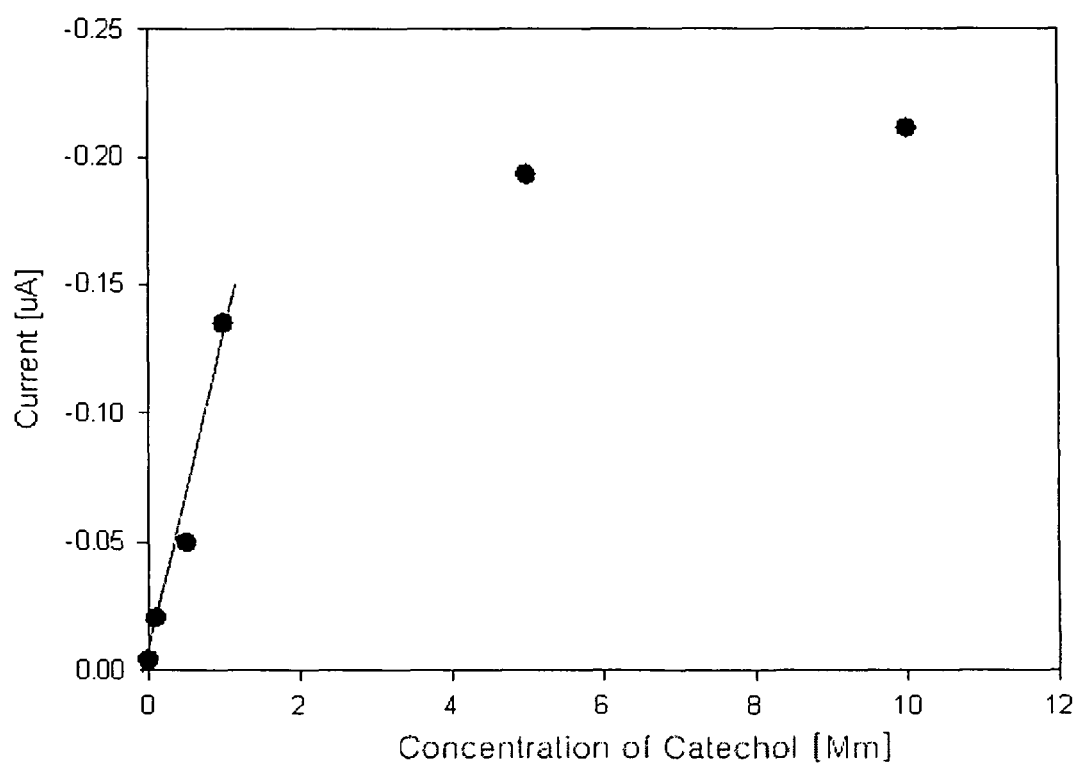
FIG. 5 depicts a graph of the current variation of a tyrosinase enzyme electrode depending on the concentration of catechol introduced into the electrode

FIG. 5 is a graph depicting current variation of the tyrosinase enzyme electrode depending on concentration of catechol introduced into the electrode. As shown in FIG. 5, it was found that the current is linearly increased with up to about 1 mM of catechol and this continues to slope gently upward. Accordingly, the catechol concentration useful for analysis of inhibition percentages of the residual agricultural chemicals was determined to about 1 mM.

Example 3

Determination of Flow Rate in Inhibition Percentage Analysis

In order to determine the optimum flow rate in real time, the measurement of the residual agricultural chemicals, current and response time corresponding to 1 mM catechol was determined by regulating the flow rate in a range of about 0.2 to 2 mL/min using the syringe pump (21) shown in FIG. 4. A sample measured in the electrochemical cell (200) was transferred into a storage unit (240). Although the current was increased as the flow rate increased to about 1.2 mL/min, the current was conversely decreased for the flow rate exceeding about 1.2 mL/min. Therefore, the optimum flow rate for analysis of inhibition percentages of the residual agricultural chemicals was determined to be about 1.2 mL/min.

Example 4

Figure 6:
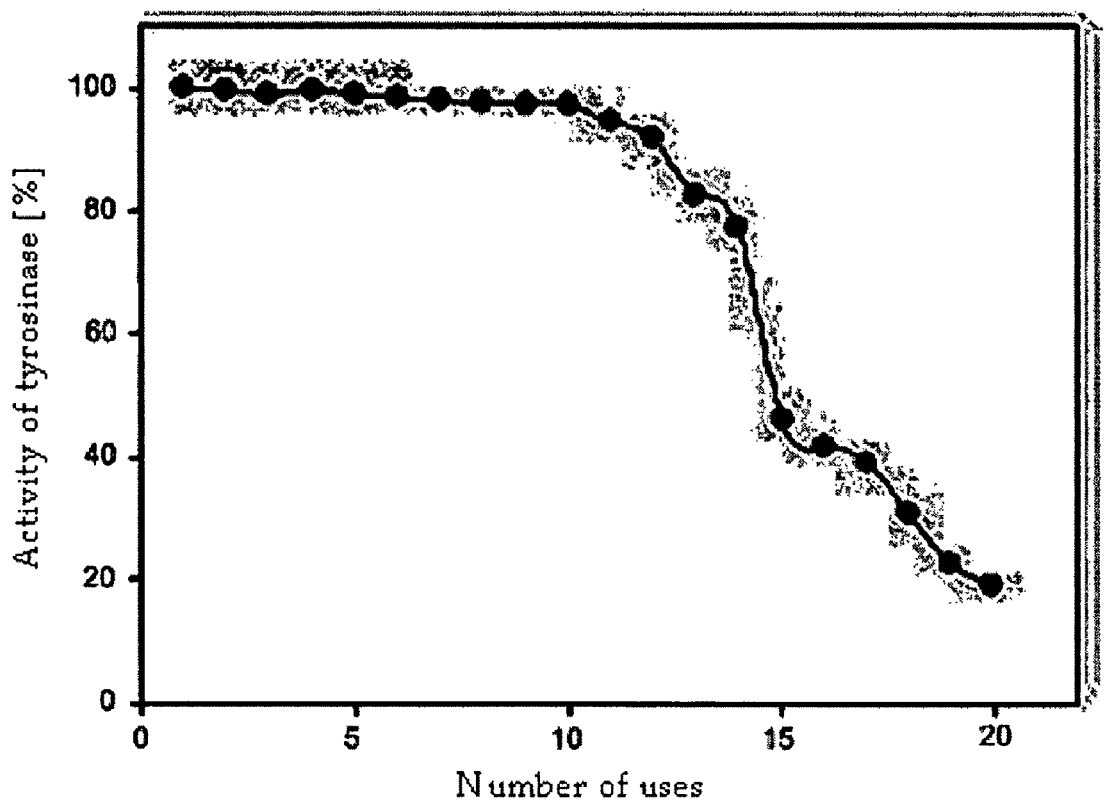
FIG. 6 is a graph depicting the variation in activities of the tyrosinase enzyme electrode containing metal nanoparticles depending on the number of uses of the electrode.

Determination of Variation in Tyrosinase Activity Depending on Number of Uses of Enzyme Electrode The tyrosinase enzyme electrode containing metal nanoparticles produced in the examples according to the present invention was subjected to measurement of variation in tyrosinase activity. According to the process described in example 3, the current for 1 mM catechol was continuously measured and the tyrosinase activities for the measured currents were compared together. As shown in FIG. 6, the activity did not decreased, but rather was constantly maintained for up to 10 uses of the electrode.

Example 5

Determination of Contact Time in Inhibition Percentage Analysis

After assembling the tyrosinase enzyme electrode containing gold nanoparticles in the flow system illustrated in FIG. 4, the contact time of the agricultural chemicals was determined by analyzing inhibition percentages of the residual agricultural chemicals under conditions of the voltage, flow rate and/or catechol concentration determined in the above examples.

The agricultural chemicals introduced into the electrode were selected from the group consisting of 2,4-dichlorophenoxyacetic acid (2,4-D), atrazine and ziram with concentration of about 0.01 ppb (parts per billion). From this experiment, it was observed that all of the above three agricultural chemicals exhibit the highest inhibition percentages at the contact time of about 200 seconds.

Example 6

Determination of Analysis Efficiency and Accuracy for Agricultural Chemicals

Figure 7:
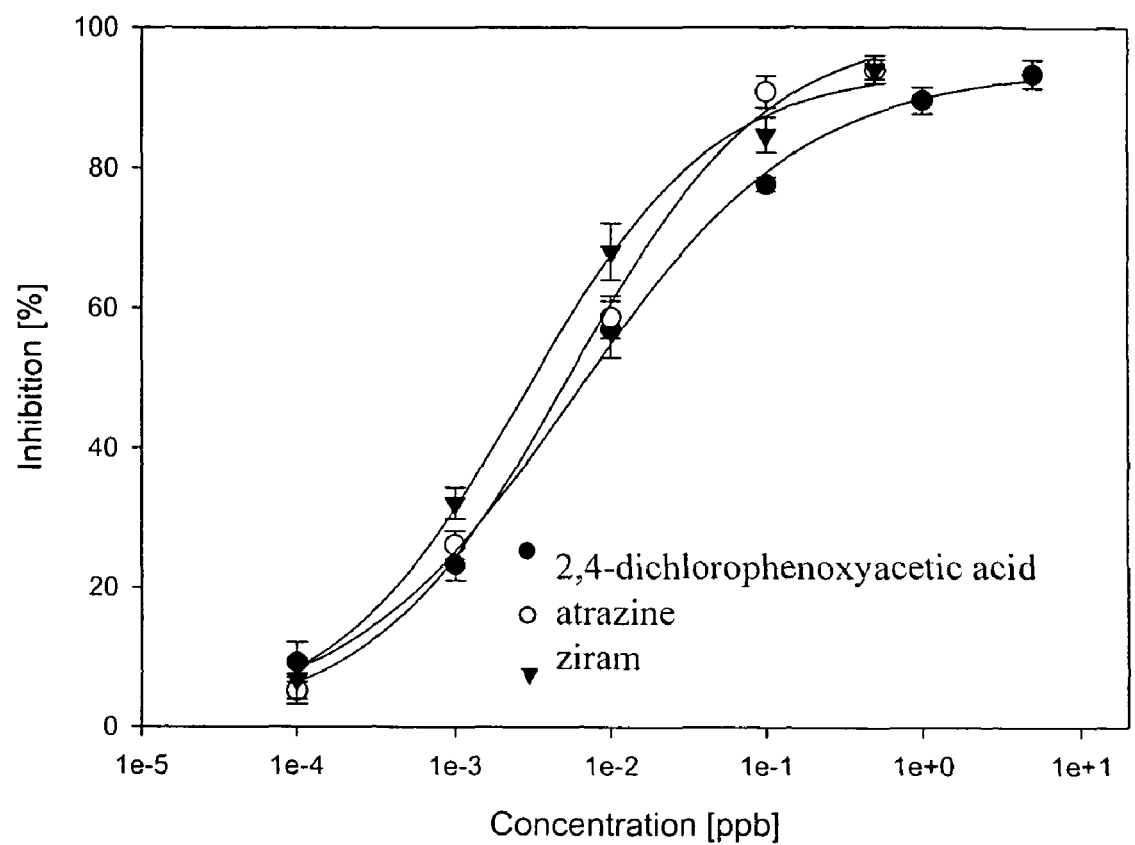
FIG. 7 is graph depicting the inhibition percentages of a tyrosinase electrode with the injection of 2,4-dichlorophenoxyacetic acid (2,4-D), atrazine and ziram in a concentration of 0.001 to 1 ppb (parts per billion) for each compound.

Example 5, the inhibition percentage was determined by introducing 2,4-dichlorophenoxyacetic acid (2,4-D), atrazine, and ziram in a concentration ranging from about 0.001 ppb to about 1 ppb to the electrode. The data in FIG. 7, demonstrates that each of the above agricultural chemicals exhibit an inhibition percentage of about 20% to about 90% in the concentration range of about 0.001 ppb to about 0.5 ppb and, there is a logarithmic correlation between the concentration and the inhibition percentage of the agricultural chemicals.

For each of the agricultural chemicals, experiments were repeated five times for each of the concentrations to calculate a relative standard deviation (RSD) thereof. The results are shown in Tables 1, 2 and 3. RSD is calculated by the following equation:

$$RSD(\%) = (\text{Standard deviation/mean value}) \times (100)$$

The term "Recovery" refers to a factor for comparison of concentrations; between the concentration of actually introduced agricultural chemicals and the concentration of agricultural chemicals measured in an enzyme electrode. Recovery is calculated by the following equation:

$$\text{Recovery }(\%) = (\text{concentration of agricultural chemicals measured in enzyme electrode/concentration of actually introduced agricultural chemicals}) \times (100)$$

TABLE 1

RSD and Recovery of 2,4-dichlorophenoxyacetic acid

| Concentration [ppb] | R.S.D (intra-assay, No. of measurements = 5) [%] | Recovery [%] |
|---|---|---|
| 0.001 | 15.0 | 83.2 |
| 0.01 | 17.1 | 110.3 |
| 0.1 | 6.5 | 114.1 |
| 1 | 4.9 | 102.3 |

TABLE 2

RSD and Recovery of atrazine

| Concentration [ppb] | R.S.D (infra-assay, No. of measurements = 5) [%] | Recovery [%] |
|---|---|---|
| 0.001 | 14.0 | 113.9 |
| 0.01 | 7.5 | 93.4 |
| 0.1 | 6.9 | 117.3 |
| 0.5 | 2.7 | 94.9 |

TABLE 3

RSD and Recovery of ziram

| Concentration [ppb] | R.S.D (infra-assay, No. of measurements = 5) [%] | Recovery [%] |
|---|---|---|
| 0.001 | 16.2 | 86.2 |
| 0.01 | 8.0 | 117.8 |
| 0.1 | 3.3 | 102.9 |
| 0.5 | 2.4 | 118.9 |

As illustrated in the above tables, RSD ranged from about 2.4% to about 17.1%. As the concentration of the agricultural chemicals was decreased, RSD was higher. Conversely, RSD was lowered when the concentration was increased. Also, recovery of the chemicals ranged from about 83.2% to about 118.9% with a mean value of about 104.6% relative to the concentration of the agricultural chemicals actually introduced to the electrode, as measured for the tyrosinase enzyme electrode containing gold nanoparticles.

Moreover, performances of the tyrosinase enzyme electrode containing gold nanoparticles according to the present invention are listed in the following tables, compared with the previously developed electrodes.

TABLE 4

Comparison of performances of tyrosinase enzyme electrodes for measurement of 2,4-dichlorophenoxyacetic acid

| Type of electrode | Substrate | Analysis time | Detection limit | Detection range | Stability | Reference document |
|---|---|---|---|---|---|---|
| Printed electrode | 50 μM catechol | — | 1.5 ppm | — | — | C. V. drine, et. al. Talanta, 59$^{th}$ vol. pp 503 (2003) |
| Gold nano-particle/ glass carbon | 1 mM catechol | 3-5 minutes | 0.55 ppt | 1 ppt-1 ppb | After 10 days, 90% | The present invention |

TABLE 5

Comparison of performances of tyrosinase enzyme electrodes for measurement of atrazine

| Type of electrode | Substrate | Analysis time | Detection limit | Detection range | Stability | Reference document |
|---|---|---|---|---|---|---|
| Polypyrrol/ glass carbon | 0.14 mM catechol | — | 0.1 ppm | 0.05-0.5 ppm | — | J. L. Besombes, et. al, Anal. Chim Act., (311), pp 255 (1995) |
| Gold | 25 μM catechol | — | 1.08 ppm | — | — | L. Campanella, et. al., Sens. Act. B., (112) pp 505, (2005) |
| Gold nano-particles/ glass carbon | 1 mM catechol | 3-5 minutes | 0.35 ppt | 1 ppt-0.5 ppb | After 10 days, 90% | The present invention |

TABLE 6

Comparison of tyrosinase enzyme electrodes for measurement of ziram

| Type of electrode | Substrate | Analysis time | Detection limit | Detection range | Stability | Reference document |
|---|---|---|---|---|---|---|
| Reversed-micelle/ graphite | 0.4 mM phenol | 2-4 minutes | 22 ppb | 61-672 ppb | — | M. El Kaoutit, et. al., Anal. Lett., (37) pp 1671 (2004) |
| Gold nano-particles/ glass carbon | 1 mM catechol | 3-5 minutes | 0.24 ppt | 1 ppt-0.5 ppb | After 10 days, 90% | The present invention |

Tables 4, 5 and 6, illustrate that a tyrosinase enzyme electrode comprising metal nanoparticles improves the detection limits in the range of ppt (parts per trillion) units. Consequently, the tyrosinase enzyme electrode containing metal nanoparticles can achieve high stability and accurate detection limits.

FIGS. 8a to 8e are cross sectional views sequentially depicting the method of making a tyrosinase enzyme, comprising the steps of: forming a metal nanoparticle layer on an electrode, the metal nanoparticle layer comprising metal nanoparticles, wherein the metal nanoparticles exist in a discrete form, wherein each of the nanoparticles is separated from adjacent nanoparticles; forming a buffer layer on the metal nanoparticle layer; forming a substrate on the buffer layer; and immobilizing a tyrosinase enzyme on the substrate.

In some embodiments the second substrate is introduced on the immobilized tyrosinase and in some embodiment the additionally introduced substrate is pyrroloquinoline quinone.

Figure 8A:
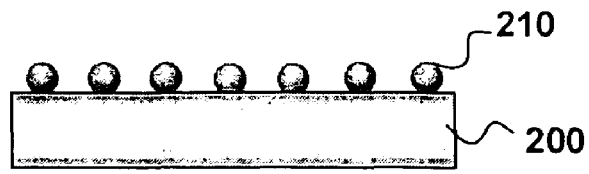
Figure 8B:
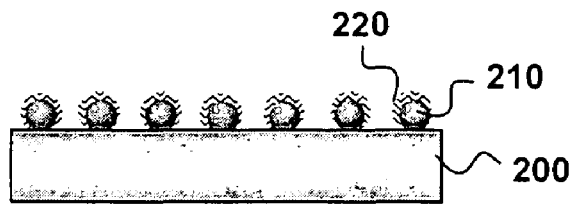
Figure 8C:
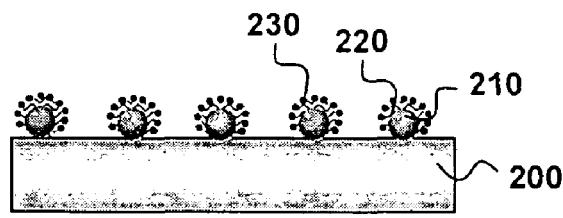

Some embodiments of this process are further described below. In FIGS. 8a to 8b, a nanoparticle layer (210) is formed on a support (200) by the method previously described. In some embodiments of the present invention the nanoparticle layer comprises gold nanoparticles. A buffer layer is formed on the nanoparticle layer (210) with the same procedure and composition as described herein. Referring to FIG. 8c, a substrate (230) is bound on the support (200) with the buffer layer (220). The substrate (230) is used for a tyrosinase enzyme. Accordingly, a substrate (230) is, in some embodiments of the present invention, pyrroloquinoline quinone (PQQ).

Figure 8D:
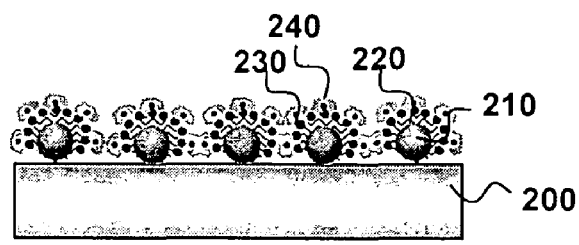

In some embodiments the bound substrate (230) is formed on the buffer layer (220) by adding about 1 mL of HEPES buffer solution with about 1 mg of PQQ, about 0.2 M EDC (N-ethyl-3-(dimethylaminopropyl)carbodiimide-HCl) and about 0.2 M NHS (N-hydroxy succinimide) to a support (200) and incubating for 12 hours in darkness. Referring to FIG. 8d, a tyrosinase enzyme (240) is immobilized on the substrate (230) bound on the support (200). For example, a combined solution including about 0.2 M EDC (N-ethyl-3-(dimethylaminopropyl)carbodiimide-HCl), about 0.5 M NHS (N-hydroxy succinimide), and about 1 mg of tyrosinase is added to a support (200) followed by incubation at 4° C. for 24 hours.

Figure 8E:
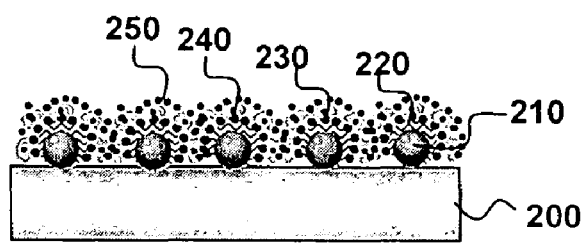

Also, a second substrate (250) is introduced on the immobilized tyrosinase enzyme (240) as demonstrated in FIGS. 8a to 8e. That is, a substrate (250) in addition to the substrate (230) illustrated in FIG. 8c. FIG. 8c depicts the introduction of a new substrate (250) to a tyrosinase enzyme (240). In FIG. 8e, the second substrate (250) is PQQ as shown in FIG. 8c. The binding method of PQQ is illustrated in FIG. 8c.

In some embodiments tyrosinase enzyme (240) (see FIGS. 8a to 8e) immobilized electrode contains a substrate (230) and a second substrate (250). A suitable substrate should be supplied for an enzyme activation and an enzymatic reaction. In some embodiments of the present invention, an enzyme is activated by the presence of the bound substrate without an external supply of substrate. The tyrosinase enzyme electrode can therefore easily analyze residual agricultural chemicals or pesticides contained in a subject or sample.

In some embodiments of the present invention, a tyrosinase electrode can be produced as described above. Using the PQQ bound electrode and the tyrosinase immobilized PQQ bound electrode, the currents were compared before and after the contact of the agricultural chemicals.

Herein, the inhibition percentage is calculated by the following equation 2:

Inhibition (%)={(current at the tyrosinase immobilized PQQ bound electrode before the addition of agricultural chemicals−current at the tyrosinase immobilized PQQ bound electrode after the addition of agricultural chemicals)/(current at the tyrosinase immobilized PQQ bound electrode before the addition of agricultural chemicals−current at the PQQ bound electrode before the addition of agricultural chemicals)}×(100)

Example 7

Determination of Current Variations in the Presence of Agricultural Chemicals

Using the tyrosinase enzyme electrode depicted in FIGS. 8a to 8e, the current variations were measured before and after the contact of 2,4-D.

FIG. 9 is a graph depicting current variation of a tyrosinase enzyme electrode depending on the presence of the residual agricultural chemicals according to the Example 2. Referring to FIG. 9, a solid line represents the current at the tyrosinase electrode in a phosphate buffer solution (PBS) before the addition of 2,4-D and a dotted line was the current at the tyrosinase electrode after the addition of about 100 ppb of 2,4-D. The currents were measured by differential pulse voltammetry. As shown in the FIG. 9, the highest current change before and after the addition of 2,4-D was observed at about 0.1 V. After changing a PBS solution, the current at the tyrosinase electrode was recovered even though the exposure to 2,4-D. That is, reproducibility of the inhibition measurement using the enzyme electrode was confirmed.

Example 8

Determination of Current Variations Dependent on the Concentration of Agricultural Chemicals The current variations were measured depending on the concentration of 2,4-D using the tyrosinase immobilized PQQ bound gold nanoparticles deposited electrode. FIG. 10 is a graph depicting current variations of a tyrosinase enzyme electrode depending on the concentration of 2,4-D according to a second description of the present invention. FIG. 11 is a graph depicting inhibition percentage of a tyrosinase enzyme electrode depending on the concentration of a residual agricultural chemical under a constant flow. Referring to FIG. 10, the currents at about 0.1 V decreased as the concentration of 2,4-D increased.

Referring to FIG. 11, inhibition percentage depending on the concentration of 2,4-D under about 1.2 mL/min of flow rate was illustrated. The contact time was within about 5 min. A linear relationship between the inhibition percentage and the concentration of 2,4-D was shown at about 0.5 ppt. to about 10 ppt. Also, repeated measurements were conducted, whereby six measurements were conducted under the same condition to check the reproducibility. From the repeated measurements, an inhibition graph was obtained. It was observed that the tyrosinase enzyme electrode produced by the method of the present invention has a reproducibility in the determination of agricultural chemicals under a constant flow.

Example 9

Measurements of Residual Agricultural Chemicals Using a Miniaturized Enzyme Electrode A miniaturized enzyme electrode was produced by applying the electrode materials on a support. That is, a miniaturized conductive carbon electrode was formed on a support by vacuum-metallizing or plating and metal nanoparticle, self-assembled monolayer, PQQ, and tyrosinase was introduced on the electrode. Also, the measurements of residual agricultural chemicals were conducted using the miniaturized enzyme electrode.

FIG. 12 is a graph depicting inhibition percentage of a miniaturized tyrosinase enzyme electrode with the injection of 2,4-D in a concentration of about 0 ppt to about 50 ppt (parts per trillion). FIG. 12 represents the concentration range of 2,4-D which was about 0 ppt to about 50 ppt and confirmed by three-repeated measurements. The current decreased as the concentration of 2,4-D increased and a constant current appeared over about 10 ppt. From the repeated experiments, the changes in the inhibition percentage was not significant.

In some embodiments of the present invention, a nanoparticle layer was formed on the electrode and a buffer layer was formed on the surface of nanoparticle using alkanethiol having a carboxyl group (3-mercaptopropionic acid). Also, a substrate PQQ was bound on the buffer layer by covalent bond and tyrosinase was immobilized on the substrate. Accordingly, the substrate bound tyrosinase electrode is applied in the measurements of the residual agricultural chemicals without an external supply of substrate.

As described above, the tyrosinase enzyme electrode containing metal nanoparticles according to the present invention has advantages in that it can considerably improve detection limits, analyze residual agricultural chemicals present even in a small amounts without the need to pre-treat the sample to be measured, and rapid analysis of results.

While the present invention has been described with reference to examples and embodiments, these are intended to illustrate the invention and do not limit the scope of the present invention. It will be obvious to those skilled in the art that various modifications and/or variations may be made therein without departing from the spirit and scope of the present invention.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A tyrosinase enzyme electrode comprising:
   an electrode;
   a metal nanoparticles layer formed on the electrode;
   a buffer layer formed on the nanoparticle layer;
   a substrate for an enzyme activation bound on the buffer layer;
   a tyrosinase enzyme immobilized on the substrate, and
   an additional substrate over the tyrosinase enzyme, wherein the additional substrate comprises pyrroloquinoline quinine.

2. The electrode according to claim 1, wherein the metal nanoparticle layer comprises metal nanoparticles in a discrete form in that each of the metal nanoparticles is separated from adjacent nanoparticles, and the nanoparticles comprise a metal selected from the group consisting of gold, silver, copper, palladium and platinum.

3. The electrode according to claim 1, wherein the buffer layer comprises alkanethiol compounds having a functional group selected from carboxyl group, amino group, hydroxyl group and sulfonic acid group.

4. The electrode according to claim 1, wherein the electrode is made of glassy carbon.

5. A method for fabrication of tyrosinase enzyme electrode comprising:
   forming a metal nanoparticles layer on an electrode, in which metal nanoparticles exist in a discrete form in that each of the nanoparticles is separated from adjacent particles;
   forming a buffer layer on the metal nanoparticle containing layer;
   forming a substrate for an enzyme activation on the buffer layer;
   immobilizing a tyrosinase enzyme on the substrate, and
   introducing an additional substrate over the immobilized tyrosinase enzyme, wherein the additionally introduced substrate is pyrroloquinoline quinone.

* * * * *